United States Patent
Varma et al.

(10) Patent No.: US 7,695,674 B2
(45) Date of Patent: Apr. 13, 2010

(54) METHOD OF STERILIZING BALLOON WITH IONIZING RADIATION

(75) Inventors: Ashish Varma, Galway (IE); Frank Clarke, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 895 days.

(21) Appl. No.: 10/671,946

(22) Filed: Sep. 29, 2003

(65) Prior Publication Data

US 2005/0069452 A1    Mar. 31, 2005

(51) Int. Cl.
*A61L 2/08*    (2006.01)
(52) U.S. Cl. .......................... 422/23; 422/22; 206/439
(58) Field of Classification Search .................... 422/1, 422/2, 22, 23, 40; 604/96.01, 915; 206/439
See application file for complete search history.

(56) References Cited

U.S. PATENT DOCUMENTS

| | | |
|---|---|---|
| 4,179,338 A | 12/1979 | Gordon |
| 4,616,046 A | 10/1986 | Kornbaum et al. |
| 4,778,656 A | 10/1988 | Allen et al. |
| 4,813,210 A | 3/1989 | Fukui et al. |
| 5,014,494 A | 5/1991 | George |
| 5,137,688 A | 8/1992 | DeRudder |
| 5,417,969 A | 5/1995 | Hsu et al. |
| 5,554,120 A | 9/1996 | Chen et al. |
| 5,577,368 A | 11/1996 | Hamilton et al. |
| 5,881,534 A | 3/1999 | Ward et al. |
| 6,461,630 B1 | 10/2002 | Tucker et al. |
| 6,520,323 B1* | 2/2003 | Colombo ................ 206/213.1 |
| 2003/0083616 A1 | 5/2003 | Wantink et al. |
| 2005/0194723 A1* | 9/2005 | Muratoglu et al. .......... 264/488 |
| 2006/0260967 A1* | 11/2006 | Clarke et al. ................ 206/438 |

FOREIGN PATENT DOCUMENTS

WO    WO 2004/064618    8/2004

* cited by examiner

*Primary Examiner*—Elizabeth L McKane

(57) ABSTRACT

A sterilization process that preserves the mechanical properties of dilatation balloons and balloon catheters manufactured from polymers susceptible to the degradation reactions induced by ionizing radiation. The advantages of the sterilization process contemplated by this invention results from a reduced oxygen environment during sterilization, thereby preventing the degeneration process initiated in polymers during irradiation. Additionally, a balloon or balloon dilatation catheter sterilized by the process of the invention is provided.

16 Claims, 1 Drawing Sheet

METHOD OF STERILIZING BALLOON WITH IONIZING RADIATION

BACKGROUND OF THE INVENTION

1. Field of the Invention

This invention relates to intravascular balloon catheters and, in particular, the use of ionizing radiation for the sterilization of such devices.

2. Background Art

Surgical procedures employing balloons and medical devices incorporating those balloons (i.e., balloon catheters) have become routine. These procedures, such as angioplasty procedures, are conducted on narrow or obstructed openings in blood vessels, and other passageways in the body, to increase the flow through the obstructed areas. For example, in an angioplasty procedure, a dilatation balloon catheter is used to enlarge or open an occluded blood vessel which is partially restricted or obstructed due to the existence of a hardened stenosis or buildup within the vessel. This procedure requires that a balloon catheter be inserted into the patient's body and positioned within the vessel so that the balloon, when inflated, will dilate the site of the obstruction or stenosis so that the obstruction or stenosis is minimized, thereby resulting in increased blood flow through the vessel.

Measurable characteristics of balloons in general, and more specifically of dilatation balloons, include distensibility (the percent radial expansion with increased pressure), elastic stress response (repeatability of obtaining the same diameter at the same pressure during repeated inflation-deflation cycles), flexibility, tensile strength and optical clarity.

Polymeric materials are increasingly being used to manufacture balloons, particularly dilatation balloons. It has been found that balloons can be formed by processing a polymeric material composed of polymer chains having sufficient regions of molecular structure with inter-molecular chain interaction to ensure the integrity and strength of the structure, as well as sufficient regions which permit sections of the polymer chains to "uncoil" to permit growth. Such balloons are (i) sufficiently distensible (i.e., about 5 to about 20%) to allow treatment of various sized arteries, (ii) have a high degree of elastic stress response (i.e., less than about 5.00), which permits the physician to treat multiple stenosis within the same artery without having to be concerned with increasing balloon diameter after repeated inflations, and (iii) have strength sufficient to treat hardened stenosis (i.e., greater than about 14,000 psi). Therefore, balloons formed by such methods have an overall advantageous combination of these physical properties i.e., distensibility, elastic stress response and tensile strength, that are superior to those exhibited by other balloons of the related art. The sterilization method of the present invention may be used with balloons made from any material that is degraded by radiation doses typically used in ionizing radiation sterilization.

While the foregoing properties are desirable in balloons, these attributes are typically adversely affected by the sterilization process which all balloons and balloon catheters must be subjected to prior to use in the human body. For example, when a balloon is exposed to a traditional sterilization process (e.g., humidity of 60±15%, temperature of about 45±5° C., 100% ethylene oxide for approximately 12-16 hours) the balloon tends to shrink, which causes a corresponding increase in wall thickness. This increase in wall thickness will adversely affect the folded profile of the sterilized balloon product. Furthermore, the distensibility of many balloons is adversely affected by the sterilization processes currently used in the art. Therefore, it is desirable that any sterilization process used to treat balloons and balloon catheters provide adequate sterilization, while at the same time not adversely affecting the physical characteristics of the finished balloon or balloon catheter product.

Ethylene oxide sterilization is one method for sterilization of heat-sensitive or moisture-sensitive medical instruments including dilatation balloons and dilatation balloon catheters. However, there are several disadvantages to using ethylene oxide as a method for sterilization. Ethylene oxide is highly flammable and explosive in air and must be used in an explosion-proof sterilizing chamber in a controlled environment. Ethylene oxide is also readily absorbed by many polymers and is not always easily desorbed or eliminated. Toxic emissions and residues of ethylene oxide present hazards to personnel, patients and the environment. Furthermore, the processing conditions employed during the ethylene oxide sterilization process can alter the composition and morphology of some polymeric materials, and hence their mechanical properties.

Sterilization of polymeric medical devices by ionizing radiation is increasingly being employed as an alternative to gaseous ethylene oxide sterilization. The term ionizing radiation is used to designate the emission of electrons or highly accelerated, relatively heavy, nuclear particles such as protons, neutrons, alpha particles, deuterons, beta particles, or their analogs, directed in such a way that the particle is projected into the mass to be irradiated. Radiation sterilization includes the use of ultraviolet rays, electron beams, x-rays, gamma rays, and to a limited extent, gas plasma and microwave radiation. Sterilization by ionizing radiation is usually carried by using either gamma radiation, from Cobalt or Cesium sources, or electron beam (E-beam) irradiation. One difference between the two sources is the dose rate or exposure time over which the dose is delivered. The dose rate for E-beam irradiation can be as high as 20 kGy/s compared to 1-10 kGy/hrs for Gamma radiation. Hence the exposure times are often considerably shorter for E-beam sterilization than for sterilization by gamma radiation.

Sterilization by ionizing radiation is a consequence of the high-energy electrons released from the interaction of Gamma-ray photons or electron-beam particles with the material being sterilized. Depending on the energy of radiation many secondary electrons and free radicals can be created in the vicinity of the original interaction site. The cascade is propagated until all the excess energy above the ionization threshold is dissipated. Thus, from a single incoming photon or electron, a shower of secondary electrons is generated. These high-energy electrons permanently alter the DNA sequences in the microbiological species, rendering them innocuous.

However, the high-energy photons and electrons can also initiate unwanted ionization events in polymeric material during sterilization. The effects vary greatly with the chemical structure of the polymer and the employed dose of radiation. Alterations in molecular structure, caused by the ionization processes, are manifested as changes in physical and mechanical properties of the polymer. The two major mechanisms of degradation that occur during the irradiation process are: (1) chain scission of the polymer molecule resulting in a reduction in molecular weight and (2) cross-linking of the polymer molecules which can lead to the formation of three dimensional network structures. The chemical composition of the polymer largely dictates the degradation mechanism, although the two mechanisms can sometimes occur simultaneously with the final properties being dictated by the net-effect.

The degradation process is initiated when high-energy radiation interacts with the hydrocarbon polymeric molecule to generate macro-radicals, shown in the following reaction, where R—H is the polymer molecule and R˙ is the "cleaved" polymer chain which forms during irradiation:

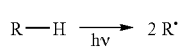   Step 1: Initiation

Polymeric macro-radicals (R˙) rapidly combine with environmental oxygen, which is a very efficient radical scavenger, to form peroxide radicals as shown by the following reaction:

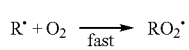   Step 2: Propagation

Polymeric peroxide radicals (RO$_2$˙) can then react with another hydrocarbon polymeric molecule to further propagate the degradation process:

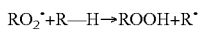   Step 3: Propagation

Whilst a polymeric macro-radical (R˙) can react again with oxygen as in step 2, the hydroperoxide (ROOH) may also decompose to form additional radicals, thus propagating the degradation process further:

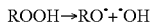   Step 4: Propagation

As a result of the auto-catalytic nature of the oxidation process, a single primary event can lead to extensive damage by generating a cascade of radicals from the initial radicals created during the irradiation process.

In relation to the sterilization of polymeric materials, ionizing irradiation has been found to have a negative impact on the properties of dilatation balloons manufactured from certain polymers, such as polyamide block copolymers. Resultant physical changes can include embrittlement, discoloration, odor generation, stiffening, softening, enhancement of chemical resistance, and an increase or decrease in melt temperature. Various high-performance stabilizers have been found to be ineffective in preserving the physical properties of these polymers, probably due to high rates of the degradation reactions. Therefore, alternative methods and devices are needed to minimize the damage caused by ionizing radiation during sterilization of susceptible polymers.

SUMMARY OF THE INVENTION

It is an aspect of this invention to provide an improved sterilization method for balloons which will not adversely affect the physical properties of the balloons.

It is a further aspect of this invention to provide a sterilized balloon and sterilized balloon catheter in which certain desired properties are preserved following sterilization by ionizing radiation.

It is a further aspect of the invention to provide an apparatus for sterilizing balloons with ionizing radiation while preserving their desired physical properties.

Still another aspect of this invention is to provide a method whereby the environmental oxygen content is reduced during sterilization of balloons by ionizing radiation, thereby preventing and attenuating degradation reactions of polymeric materials.

These aspects, as well as others, which will become apparent from the description which follows, are achieved by subjecting balloons and balloon catheters susceptible to degradation reactions to a novel sterilization process.

The present invention contemplates a novel sterilization process for balloons manufactured from polyamide block copolymers or other polymers susceptible to degradation reactions induced by ionizing radiation. To reduce environmental oxygen content, balloons and balloon catheters of the invention are packaged in a pouch capable of maintaining a low level of oxygen and a sterile environment within said pouch. The novel sterilization process also contemplates subjecting balloons and balloon catheters of the invention packaged in a pouch of the invention to an inert gas (e.g., nitrogen) to reduce oxygen content. The novel sterilization process does not adversely affect balloon properties typically compromised by ionizing radiation of polymeric balloons.

It should be understood that the foregoing description of the invention is intended merely to be illustrative and that other embodiments and modifications may be apparent to those skilled in the art without departing from the spirit and scope of the invention.

DETAILED DESCRIPTION OF THE INVENTION

Figure 1:
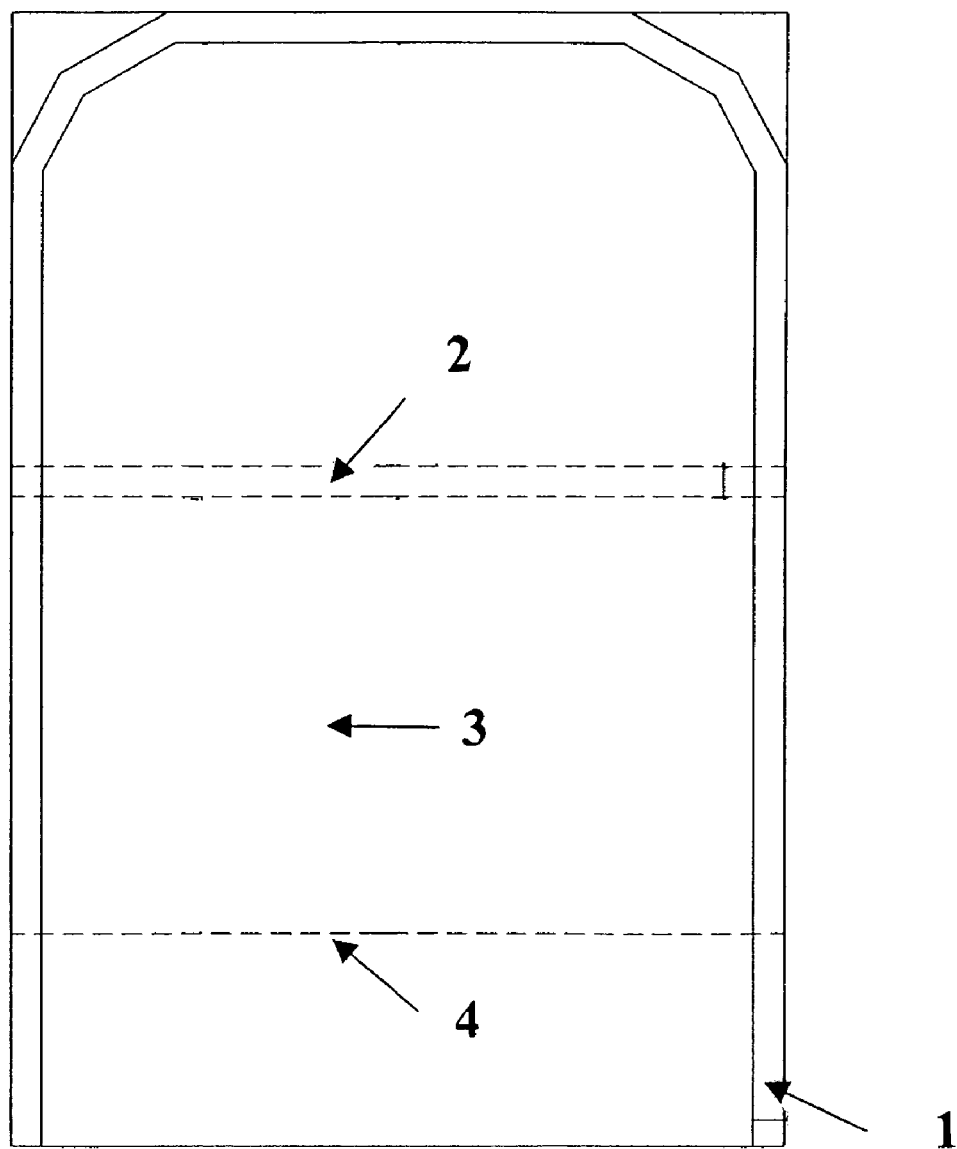
FIG. 1 shows a preferred pouch suitable for use with the present invention.

The present invention provides a novel method of sterilization by ionizing radiation which will not adversely affect, to any significant degree, the desirable properties of dilatation balloons manufactured from polymers susceptible to degradation reactions.

The balloons used in the novel sterilization process include balloons made from polymeric materials comprising regions of crystalline and rubbery material, referred to as "hard" and "soft" segments respectively.

Examples of polymeric materials which have these alternating zones or regions include block copolymers, and physical mixtures of different polymers. Examples of block copolymers which may be used include polyester block copolymers, polyamide block copolymers and polyurethane block copolymers, and mixtures thereof. Examples of the mixtures which may be used include mixtures of nylon and polyamide block copolymers and polyethylene terephthalate and polyester block copolymers. The preferred block copolymer which can be used in accordance with the method of this invention is polyamide block copolymer. Commercially available polyamide block copolymers for use in the manufacture of balloons used in this invention include PEBAX® material available from Atofina Chemicals, Inc. (Philadelphia, Pa.), VESTAMID® material available from Huls America, Inc. (Piscataway, N.J.), and GRILON® material available from EMS-Chemie AG (Domat/EMS, Switzerland).

In order to preserve the desirable properties of such a balloon during sterilization by ionizing radiation, the balloon must be subjected to the novel sterilization process contemplated by the present invention. The primary objective of the stabilization method is to reduce the oxygen concentration in the immediate environment of the susceptible polymer and product.

This is done by packaging the product in a pouch that provides a barrier to atmospheric oxygen and also maintains a sterile environment, and that optionally comprises an oxygen absorber. The latter, although not essential, helps to maintain the reduced level of oxygen. A preferred pouch may be made, for example, of a first layer comprising a material such as 12μ PET, 25.4μ WPE/Foil/Adhesive and 50μ Clear EZ PEEL® material; a second layer comprising a material such as 2FS Uncoated TYVEK ® material, porosity 18-240 seconds by the Gurley porosimeter test (100 cc of air to pass through 1 square inch of TYVEK®material); and a third layer comprising a material such as 12μ PET, 25.4μ WPE/Foil/Adhesive and 50μ Clear EZ PEEL® material (a fully coextruded ,nylon-core top web system available from Perfecseal Ltd., Springtown Industrial Estate, Londonderry, BT48 0LY, Northern Ireland, UK); wherein the second layer is between the first and third layer. TYVEK® material is commercially available from DuPont and consists of multiple spun woven extruded polyethylene strands, compressed under high pressure to form a complex system of microscopic porous channel which provides a tortuous path within a thin flexible opaque sheet. An alternative pouch comprising two layers of material such as 12μ PET, 25.4μ WPE/Foil/Adhesive and 50μ Clear EZ PEEL® may be used with the present invention when, for example, the oxygen absorber is not used.

FIG. 1 shows a preferred pouch suitable for use with the present invention. The preferred outer dimensions of the pouch are 250 mm±2 mm and 375 mm±2 mm. A sealed rim 1 about the outer edges of the first layer and third layer, preferably 10 mm±2 mm in width, forms a sealed interior space. An optional seal line 2, preferably 10 mm±2 mm in width, creates a second sealed interior space 3 to accommodate an oxygen absorber. The oxygen absorber may be inserted through a pouch lip 4 preferably positioned 70 mm±2 mm from the outer edge of the pouch.

The above-mentioned oxygen absorber includes a variety of known materials such as those containing iron or a compound of iron, such as iron hydroxide, iron oxide, iron carbide, etc., as an active component. Typical commercial products of this type are AGELESS (manufactured by Mitsubishi Gas Chemical), MODURAN (manufactured by Nippon Kayaku), and SECUR (manufactured by Nippon Soda). The oxygen absorber shall be capable of withstanding a sterilization procedure by means of ionizing irradiation without being impaired and can be accommodated together with the pouch of the invention as is, or as prepackaged in a gas-permeable small bag.

In a preferred method of the invention, nitrogen gas flush and vacuum draw are used to reduce environmental oxygen content according to the following conditions described in example 1 below.

In accordance with this invention, the oxygen levels in the immediate environment of the susceptible polymer within the pouch are reduced to prevent and attenuate degradation reactions during ionizing radiation sterilization. It is preferred that the resulting oxygen content within the pouch is less than about 10%. Typically, the oxygen content is between about 5% and about 10%. Most preferably, the oxygen content is less than about 1%. Nitrogen flush pressure is typically about 10 psi, with higher pressures near about 30 psi preferred to achieve oxygen levels below about 1%.

The sterilization method of the invention further comprises the use of ionizing radiation as a safer and more economic alternative to ethylene oxide sterilization. Sterilization by ionizing radiation can be performed by gamma irradiation, from Cobalt or Cesium sources, or electron beam (E-beam) irradiation. An example of a preferred method for ionizing irradiation comprises exposure to E-beam irradiation at about 50 kGy.

The sterilization process is an important factor in determining the final physical characteristics of the balloons and balloon catheters of this invention. Therefore, the novel sterilization process is necessary to ensure a clinically useful and safe finished balloon and balloon catheter with preserved mechanical properties superior to those exhibited by the balloons sterilized with conventional methods.

EXAMPLE 1

A pouch was made of a first layer comprising 12μ PET, 25.4μ WPE/Foil/Adhesive and 50μ Clear EZ PEEL® material; a second layer comprising 2FS Uncoated TYVEK® material, porosity 18-240 seconds by the Gurley porosimeter test (100 cc of air to pass through 1 square inch of TYVEK® material); and a third layer comprising 12μ PET, 25.4μ WPE/Foil/Adhesive and 50μ Clear EZ PEEL® material; wherein the second layer was between the first and third layers.

The Oxygen level within the pouch is reduced by a combination of nitrogen flush and vacuum draw-down with the final value being determined by the pressures and the times used in the evacuation and flushing processes. The actual sealing/flushing conditions used for this trial were as follows:

Sealing pressure: 90 psi (±10)
Sealing temperature: 150° C. (±10)
Dwell time: 3 seconds (±1)
Nitrogen flush time: 9 seconds (±1)
Nitrogen flush pressure: 10 psi
Vacuum time: 3 seconds (±1)

These settings were found to give % oxygen levels between 5 and 11%. For comparison, samples were also packaged in standard TYVEK ® material EtO pouches (these packages do not provide an Oxygen barrier) and irradiated at the E-beam dose level mentioned below. The impact of sterilization process on the mechanical properties of the balloons was evaluated by measuring the pressure required to burst the balloons.

EXAMPLE 2

Polyamide block copolymer balloons were packaged in a pouch as set forth in Example 1 and sterilized using E-beam dose of 50±8% KGy.

EXAMPLE 3

The following example demonstrates the improved balloon strength obtained by sterilization methods of this invention. Samples of polyamide block copolymer balloons were packaged as described in Example 1 or in standard Tyvek® material pouches. The balloons were subjected to the sterilization process contemplated by this invention and described in Example 2.

The mean burst pressure and the confidence interval (CI) from the total number of trials (n) are compared below. The mean burst pressure was determined at 37° C. These results demonstrate the improved balloon strength achieved by E-beam sterilization at low oxygen levels.

|  | Mean Burst Pressure (atm) ± standard deviation | 95:99 C.I. |
| --- | --- | --- |
| E-beam sterilization described in Example 2 + pouch described in Example 1 | 18.21 ± 0.62 (n = 20) | 16.17 |
| E-beam sterilization | 16.91 ± 0.55 | 15.08 |

-continued

| | Mean Burst Pressure (atm) ± standard deviation | 95:99 C.I. |
|---|---|---|
| described in Example 2 + standard Tyvek ® material pouch | (n = 19) | |

These data show that limiting the oxygen available for propagating degradation reactions can reduce the negative impact on the mechanical properties of polyamide block copolymer balloons sterilized with ionizing radiation. The improvements in mechanical properties were obtained at oxygen levels of 5-11% within the packaging. Further improvements in balloon properties may be achieved by reducing the oxygen levels to below about 1%. This preferred level of oxygen may be obtained by, for example, increasing the nitrogen flush pressure maximum to about 30 psi. Some stabilizers that are ineffective at atmospheric oxygen levels, and have enhanced performance at lower oxygen levels, can be incorporated with this invention to reduce the negative impact of ionizing radiation on mechanical properties even further.

What is claimed is:

1. A method of sterilizing a balloon susceptible to degradation by ionizing radiation, comprising
   (a) packaging said balloon in a first sealed interior space of a pouch capable of providing a barrier to atmospheric oxygen, wherein said pouch includes a first layer including a plastics-coated foil, a second layer having a porosity of 18-240 seconds by the Gurley porosimeter test, and a third layer including a plastics-coated foil, wherein the second layer is disposed between the first layer and the third layer;
   (b) placing an oxygen absorber in a second sealed interior space of the pouch, wherein said second sealed interior space is formed by a seal line formed in the layers of said pouch;
   (c) exposing said balloon enclosed in said pouch to a nitrogen gas flush sufficient to reduce the oxygen content within said pouch to less than about 10%; and
   (d) exposing said balloon and said oxygen absorber enclosed in said pouch to ionizing radiation, wherein said ionizing radiation is either gamma radiation or electron beam radiation at a dose of no greater than about 100 kGy.

2. A method according to claim 1, wherein said balloon is part of a balloon dilatation catheter.

3. A method according to claims 1 or 2, wherein said balloon is manufactured from one or more block polymers selected from the group consisting of polyester block copolymers, polyamide block copolymers, polyurethane block copolymers, a mixture of nylon and polyamide block copolymers, and a mixture of polyethylene terephthalate and polyester block copolymers.

4. A method according to claim 1, wherein said first layer comprises 12µ PET, 25.4µ WPE/Foil/Adhesive and 50µ clear, fully coextruded, nylon-core top web system material, said second layer comprises uncoated thin flexible opaque sheet material having multiple spun woven extruded polyethylene strands forming a complex system of microscopic porous channel which provides a tortuous path therethrough, and said third layer comprises 12µ PET, 25.4µ WPE/Foil/Adhesive and 50µ clear, fully coextruded, nylon-core top web system material.

5. A method according to claim 1, wherein said oxygen content is between about 5% and about 10%.

6. A method according to claim 1, wherein said oxygen content is less than about 1%.

7. A method of sterilizing a balloon susceptible to degradation by ionizing radiation, comprising:
   (a) packaging said balloon in a first sealed interior space of a pouch capable of providing a barrier to atmospheric oxygen, wherein said pouch includes a first layer including a plastics-coated foil, a second layer having a porosity of 18-240 seconds by the Gurley porosimeter test, and a third layer including a plastics-coated foil, wherein the second layer is disposed between the first layer and the third layer;
   (b) placing an oxygen absorber in a second sealed interior space of the pouch wherein said second sealed interior space is formed by a seal line formed in the layers of said pouch;
   (c) exposing said balloon enclosed in said pouch to a nitrogen gas flush sufficient to reduce the oxygen content in said pouch; and
   (d) exposing said balloon and said oxygen absorber enclosed in said pouch to ionizing radiation, while avoiding the concomitant degradation associated with sterilization at atmospheric oxygen levels.

8. A method according to claim 7, wherein said balloon is part of a balloon dilatation catheter.

9. A method according to claims 7 or 8, wherein said balloon is manufactured from one or more block polymers selected from the group consisting of polyester block copolymers, polyamide block copolymers, polyurethane block copolymers, a mixture of nylon and polyamide block copolymers, and a mixture of polyethylene terephthalate and polyester block copolymers.

10. A method according to claim 7, wherein said first layer comprises 12µ PET, 25.4µ WPE/Foil/Adhesive and 50µ clear, fully coextruded, nylon-core top web system material, said second layer comprises uncoated thin flexible opaque sheet material having multiple spun woven extruded polyethylene strands forming a complex system of microscopic porous channel which provides a tortuous path therethrough, and said third layer comprises 12µ PET, 25.4µ WPE/Foil/Adhesive and 50µ clear, fully coextruded, nylon-core top web system material.

11. A method according to claim 7, wherein said ionizing radiation is either gamma irradiation or electron beam irradiation.

12. A method according to claim 11, wherein said gamma irradiation is the administered at a dose rate of about 1 kGy/hrs to about 10 kGy/hrs.

13. A method according to claim 11, wherein said electron beam irradiation is administered at a dose rate of no greater than about 20 kGy/s.

14. A method according to claim 7, wherein said nitrogen gas flush is administered at a pressure of less than about 10 psi and said oxygen content is less than about 10%.

15. A method according to claim 14, wherein said oxygen content is between about 5% and about 10%.

16. A method according to claim 14, wherein said oxygen content is less than about 1%.

* * * * *